(12) United States Patent
Conti et al.

(10) Patent No.: US 8,506,926 B2
(45) Date of Patent: Aug. 13, 2013

(54) [18F]-FURANOSYLPURINE DERIVATIVES AND USES THEREOF

(75) Inventors: Peter S. Conti, Pasadena, CA (US); Mian M. Alauddin, Alhambra, CA (US); John D. Fissekis, South Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 1044 days.

(21) Appl. No.: 11/836,033

(22) Filed: Aug. 8, 2007

(65) Prior Publication Data

US 2008/0056988 A1    Mar. 6, 2008

Related U.S. Application Data

(63) Continuation of application No. 10/831,626, filed on Apr. 23, 2004, now Pat. No. 7,273,600.

(60) Provisional application No. 60/465,418, filed on Apr. 25, 2003, provisional application No. 60/480,274, filed on Jun. 20, 2003.

(51) Int. Cl.
*A61K 51/00* (2006.01)
*A61M 36/14* (2006.01)

(52) U.S. Cl.
CPC ..................................... *A61K 51/00* (2013.01)
USPC ......................................... 424/1.11; 424/1.89

(58) Field of Classification Search
CPC ............................... A61K 51/00; A61M 36/14
See application file for complete search history.

(56) References Cited

U.S. PATENT DOCUMENTS

| | | | |
|---|---|---|---|
| 4,751,221 A | 6/1988 | Watanabe et al. | 514/46 |
| 5,879,661 A | 3/1999 | Conti et al. | 424/1.81 |
| 5,959,100 A | 9/1999 | Kirschenheuter et al. | |
| 6,753,309 B2 * | 6/2004 | Klecker et al. | 514/1 |
| 2002/0061279 A1 | 5/2002 | DeGrado et al. | |

OTHER PUBLICATIONS

Wright et al. (Carbhyd. Res. 1968, 6, 347-354).*
Pankiewicz et al. (J. Org. Chem. 1992, 57, 553-559).*
Van Den Boogaart et al., "Conformational analysis of 3'-fluorinated A(2'-5')A(2'-5')A fragments relation between conformation and biological activity," Eur. J. Biochem. 1994, 221, 759-768.

* cited by examiner

*Primary Examiner* — Michael G Hartley
*Assistant Examiner* — Melissa Perreira
(74) *Attorney, Agent, or Firm* — DLA Piper LLP (US)

(57) ABSTRACT

2'-Deoxy-2'-[$^{18}$F]-labeled and 3'-deoxy-3'-[$^{18}$F]-labeled purine nucleoside analogs such as [$^{18}$F]-FAA and [$^{18}$F]-FXA have been found to have desirable properties for use as imaging agents. The analogs are particularly useful for in vivo imaging of biological material including organ tissues (e.g., heart, liver, brain and kidneys) and tumors. Methods for the preparation of the [$^{18}$F]-FAA and [$^{18}$F]-FXA are also provided.

18 Claims, 7 Drawing Sheets

[18F]-FURANOSYLPURINE DERIVATIVES AND USES THEREOF

RELATED APPLICATIONS

This is a continuation of application Ser. No. 10/831,626, filed Apr. 23, 2004 now U.S. Pat. No. 7,273,600, the entire contents of which are incorporated by reference, which application claims priority to U.S. Provisional Application Ser. No. 60/465,418, filed Apr. 25, 2003, and U.S. Provisional Application Ser. No. 60/480,274, filed Jun. 20, 2003, the contents of both of which are incorporated herein by reference.

FIELD OF THE INVENTION

The present invention relates to the syntheses of [$^{18}$F]-fluoroadenosine derivatives, and to the use of such derivatives as positron emission tomography (PET) imaging agents.

BACKGROUND OF THE INVENTION

Positron emission tomography, also called PET imaging or a PET scan, is a powerful technology for studying biological processes non-invasively at the molecular level. Positron emission tomography, is a diagnostic examination that involves the acquisition of physiologic images based on the detection of subatomic particles. These particles are emitted from a radioactive substance, also known as radiolabelled PET tracers (i.e., molecules labeled with positron-emitting atoms such as positron-emitting halogens) given to the patient. The subsequent views of the human body are used to evaluate function.

PET images show the chemical functioning of an organ or tissue, unlike X-ray, CT, or MRI which show only body structure. Thus, PET imaging allows a physician to examine the heart, brain, and other organs, and is particularly useful for the detection of cancer, coronary artery disease and brain disease. For example, PET imaging is unique in its ability to determine whether a patient's heart muscle will benefit from coronary artery bypass surgery. PET imaging can also provide information to pinpoint and evaluate diseases of the brain. For example, PET imaging can show the region of the brain that is causing a patient's seizures and is useful in evaluating degenerative brain diseases such as Alzheimer's, Huntington's, and Parkinson's. Within the first few hours of a stroke, PET imaging may be useful in determining treatment therapies. PET imaging can also be used to investigate lesions such as carcinomas, and can be employed for diagnosis and staging of diseases as well as judging the efficacy of anticancer drugs.

Over the last decade, much research has been directed to exploring the radiosynthesis and in vivo pharmacology of radiolabelled antiviral and antileukemic nucleoside derivatives for use as radiotracers in PET imaging, including agents such as [$^{125}$I]-2'-fluoro-5-iodo-1-β-D-arabinofuranosylcytosine (FIAC) (Perlman, et al., *Int. J. Nucl. Med. Biol.*, 11:215-218 (1984)); [$^{125}$I, $^{131}$I, $^{123}$I]-2'-fluoro-5-iodo-1-β-D-arabinofuranosyluracils (FIAU) Misra, et al., *Appl. Radiation Isotopes*, 37:901-905 (1986)); [$^{11}$C]-N-methylacyclovir (Wilson, et al., *J. Lab. Compd. Radiopharm.*, 29:765-768 (1991)); and a [$^{18}$F] derivative of 9-[(1,3-dihydroxy-2-propoxy)methyl]guanine (DHPG) (Alauddin, et al., 206th Meeting of the American Chemical Society, Chicago, Ill., Aug. 22-26 (1993); Alauddin, et al., *Nucl Med. Biol.*, 23:787-792 (1996); Alauddin, et al., *Nucl Med. Biol.*, 26:371-376 (1999)).

Imaging of organs, tissues or cellular proliferation in vivo using radiolabeled analogs of nucleosides such as [$^{133}$I]-UdR and [$^{11}$C]-thymidine, however, is plagued by extensive catabolism of the parent compounds following intravenous administration, limiting uptake into the DNA of tumor tissues. Such catabolic events include dehalogenation, cleavage of the sugar moieties from the base, and ring opening of the base. For example, administration of [$^{125}$I] labeled FIAC results in extensive deiodination in vivo (Perlman, et al., 1984, supra). In addition, FIAU can be formed in vivo from deamination of administered FIAC (Chou, et al., *Cancer Res.*, 41:3336-3342 (1981); Grant, et al., *Biochem. Pharm.*, 31:1103-1108 (1982)). A similar situation to IUdR also exists during the metabolism of FIAU. Although FIAU is less likely than IUdR to be catabolized by enzymatic cleavage of the glycosyl-base bond, and can itself be incorporated into DNA, deiodination followed by methylation at the 5 position of the base also can occur prior to DNA incorporation (Chou, et al., (1981), supra; Grant, et al., (1982), supra).

Many fluorinated analogues of adenosine nucleoside have been synthesized and studied as potential antitumor and antiviral agents (Wright, et al., *Carbohydrate Res.*, 6:347-354 (1968); Wright, et al., *J. Org. Chem.*, 34:2932-2636 (1969); Ikehara, et al., *Tetrahedron* 34:1133-1138 (1978); Pankiewicz, et al., *J. Org. Chem.*, 57:553-559 (1992); Montgomery, et al., *J. Med. Chem.*, 35:397-401 (1992); Carson, et al., *Proc. Natl. Acad. Sci.* USA, 89:2970-2974 (1992); Takahashi, et al., *Cancer Chemother. Pharmacol* 43:233-240 (1999); Kim, et al., *J. Pharm. Chem.*, 85:339-344 (1996); Mikhailopulo, et al., *J. Med. Chem.*, 34: 2195-2202 (1991); Van Aerschot, et al., *Antiviral Res.*, 12:133-150 (1989); Smee, et al., *Antiviral Res.*, 18:151-1162 (1992)). Among these, 2'-deoxy-2'-fluoro-2-chloro-9-β-D-arabinofuranosyladenine has been found to be active against human colon tumor xenografts (Carson, supra; Takahashi, supra). The 2'-deoxy-2'-fluoroarabino compounds gained much attention as anticancer agents (Carson, supra; Takahashi, supra; Kim, supra), while the 3'-deoxy-3'-fluororibo compounds have shown antiviral activity (Mikhailopulo, et al., *J. Med. Chem.* 34:2195-2202 (1991); Van Aerschot, et al., *Antiviral Res.*, 12:133-150 (1989); Smee, et al., *Antiviral Res.*, 18:1151-1162 (1992)). However, little information is available regarding the biological properties of the xylo-derivative 3'-fluoro-9-β-D-xylofuranosyladenine (Wright, et al., *Carbohydrate Res.*, 1968; 6:347-354; Robins, et al., *J. Org. Chem.*, 39:1564-1570 (1974); Lewandowska, et al., *Tetrahedron;* 53:6295-6302 (1997)). [$^{11}$C]-adenosine monophosphate has been synthesized in order to investigate its potential use for imaging of cancer (Mathews, et al. *J. Nucl. Med.*, 43:362P (2002), and [$^{14}$C]-adenosine has been shown to be a marker for myocardial blood flow in dogs.

The synthesis of unlabeled 2'-deoxy-2'-fluoro-9-β-D-arabinofuranosyladenine involves the incorporation of fluorine in the arabino configuration at C-2 of the sugar, followed by coupling with the purine base (Wright, et al., *Carbohydrate Res.* 1968; 6:347-354; Chu et al., *Chem. Pharm. Bull.*, 37:336-339 (1989)). Another reported synthesis involves treatment of $N^6$-3',5'-trirtityladenosine with (diethylamino)-sulfur trifluoride (DAST) (Pankiewicz, et al., *J. Org. Chem.*, 57:553-559 (1992); Lewandowska, et al., *Tetrahedron*, 53:6295-6302 (1997)). However, DAST is not a suitable reagent for radiochemical synthesis of the [$^{18}$F]-labeled analog of this compound due to the unavailability of the $^{18}$F-labeled reagent and the required long reaction time.

There is thus a long-felt need in the art for a suitable partially or non-catabolized imaging agent (e.g., nucleoside analog) for use in, e.g., tumor proliferation studies with PET.

Except for limited catabolism, an ideal tracer should share the other in vivo characteristics of the nucleoside, including cell transport, phosphorylation by mammalian kinase, and incorporation into DNA. In particular, development of a partially or non-catabolized purine analog would greatly simplify imaging and modeling approaches and potentially provide higher target to background ratios due to more selective incorporation of radiotracer.

SUMMARY OF THE INVENTION

The present invention provides compositions and methods for radioimaging a targeted site within a patient's body, for use for example in cancer, cardiac and neurological imaging studies.

More specifically, one aspect of this invention provides a composition for in vivo imaging of a biological material, comprising an imaging agent in dosage unit form, wherein the unit dose comprises a sufficient amount for in vivo diagnostic imaging of a 2'-deoxy-2'-[$^{18}$F]- or a 3'-deoxy-3'-[$^{18}$F]-labeled purine analog for being detected in vivo; and a physiologically acceptable carrier or adjuvant. In one embodiment, the analog is a 2'-deoxy-2'-[$^{18}$F]-fluoro-9-β-D-arabinofuranosyl purine analog or a 3'-deoxy-3'-[$^{18}$F]-fluoro-9-β-D-xylofuranosyl purine analog. In a preferred embodiment, the analog is 2'-deoxy-2'-[$^{18}$F]-fluoro-9-β-D-arabinofuranosyladenine ([$^{18}$F]-FAA). In another embodiment, the analog is 3'-deoxy-3'-[$^{18}$F]-fluoro-9-β-D-xylofuranosyladenine ([$^{18}$F]-FXA). The [$^{18}$F]-labeled nucleoside analogs [$^{18}$F]-FAA and [$^{18}$F]-FXA have been found to have an especially desirable combination of properties for use as imaging agents, in that they exhibit limited in vivo catabolism.

Another aspect of this invention provides a method of imaging biological material in a subject, comprising administering to the subject a sufficient amount of a composition comprising a 2'-deoxy-2'-[$^{18}$F]-labeled or a 3'-deoxy-3'-[$^{18}$F]-labeled purine nucleoside analog to provide an imagable concentration of said analog in said biological material, and detecting the emissions from said radioactive fluorine, thereby forming an image of the biological material. A unit dose of imaging agent is a non-toxic amount of the 2'-deoxy-2'-fluoro-D-arabinofuranosyl purine nucleoside analog which is capable of localizing in an organ or in proliferating cells and being detected in vivo by nuclear medicine techniques, such as positron emission tomography (PET).

The methods according to this invention are useful for assessing organ function or damage. For example, in a particular embodiment, the invention provides methods for predicting risk of cardiovascular disease or disorder by imaging myocardial or vascular tissue, comprising administering to the subject a sufficient amount of a composition comprising a 2'-deoxy-2'-[$^{18}$F]-labeled or a 3'-deoxy-3'-[$^{18}$F]-labeled purine nucleoside analog to provide an imagable concentration of said analog in the myocardial or vascular tissue of the subject, and detecting said analog, thereby forming an image of the myocardial or vascular tissue. The image can then be compared to the image obtained from a normal subject (i.e., a subject free from the disease or disorder being tested for). The methods of this invention are also useful for imaging other organs such as the brain or diseased tissue such as cancer in a living subject, which allows for monitoring the treatment of disease in the subject.

The present invention further provides a general direct fluorination method for preparing fluorinated analogues of purine nucleosides by direct fluorination. In one embodiment, a method is provided for preparing [$^{19}$F]-FAA, [$^{19}$F]-FXA, [$^{18}$F]-FAA, and [$^{18}$F]-FXA.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

This invention provides a method for preparing [$^{18}$F]-labeled purine nucleoside analogs, and methods of using such analogs as PET imaging agents. More specifically, this invention provides 2'-deoxy-2'-[$^{18}$F]-fluoro-9-β-D-arabinofuranosyl purine analogs and 3'-deoxy-3'-[$^{18}$F]-fluoro-9-β-D-xylofuranosyl purine analogs for use as imaging agents. In one embodiment, the imaging agents are 2'-deoxy-2'-[$^{18}$F]-fluoro-9-β-D-arabinofuranosyladenine ([$^{18}$F]-FAA) and 3'-deoxy-3'-[$^{18}$F]-fluoro-9-β-D-xylofuranosyladenine ([$^{18}$F]-FXA).

I. Synthetic Methods

Figure 1:
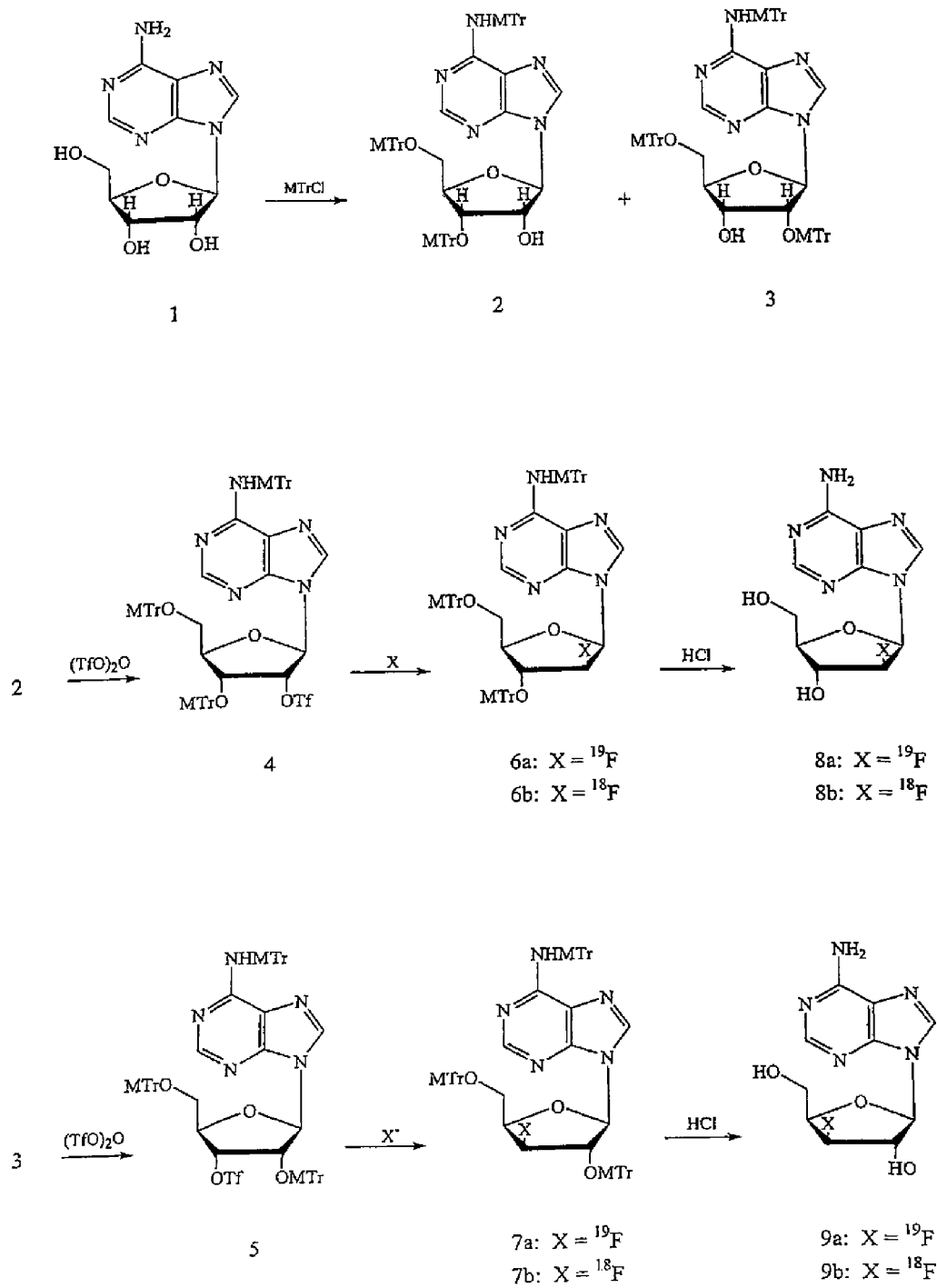
FIG. 1 shows the reaction scheme for the synthesis of [$^{18}$F]-fluoroadenosine analogues.

In general, 2'-deoxy-2'-[$^{18}$F]-fluoro-9-β-D-arabinofuranosyl purine and 3'-deoxy-3'-[$^{18}$F]-fluoro-9-β-D-xylofuranosyl purine analogs may be prepared using the reaction routes and synthesis schemes as described below. The syntheses of representative analogs [$^{19}$F]-FAA, [$^{19}$F]-FXA, [$^{18}$F]-FAA and [$^{18}$F]-FXA by direct fluorination are shown in FIG. 1. Compounds 2 and 3 were prepared from adenosine following a literature method (Pankiewicz, et al., *J. Org. Chem.* 57:553-559 (1992)). Reaction of adenosine with methoxytrityl chloride in pyridine produced a mixture of 3 compounds, which were separated by column chromatography. The early eluting compound (not shown), a methoxytrityl derivative of adenine, was discarded. The remaining products (compounds 2 and 3) were isolated in 28% and 50% yields, respectively. Both compounds were characterized by $^1$H NMR spectroscopy.

Compounds 4 and 5 were prepared in separate reactions by the reaction of compounds 2 and 3, respectively, with trifluoromethanesulfonic acid anhydride in pyridine at low temperature. Yields in this step were quite high, about 90% for both compounds. These compounds were characterized by $^1$H and $^{19}$F NMR spectroscopy, and high resolution mass spectrometry. $^{19}$F NMR spectra showed a singlet at −73.16 and −73.58 ppm for compounds 4 and 5, respectively.

Fluorination of the triflate precursor 4 with n-Bu$_4$NF produced the desired 2'-deoxy-2'-fluoro-9-β-D-arabinofuranosyladenine derivative 6a in 20% yield, and reaction of the triflate precursor 5 with n-Bu$_4$NF produced the corresponding 3'-deoxy-3'-fluoro-9-β-D-xylofuranosyladenine derivative 7a in 50% yield. The low yield of compound 6a compared to compound 7a may be due to steric hindrance exerted by the purine ring. Both compounds were purified, and characterized by $^1$H and $^{19}$F NMR spectroscopy and high-resolution mass spectrometry. The $^{19}$F NMR spectrum of compound 6a was more complex compared to that of 7a, which was a clean doublet of triplet, due to a long range coupling between the 2'-fluorine and C$_8$H in compound 6a (J=~1 Hz). Furthermore nucleophilic substitution of the 2'-(ribo)triflate of adenosine with acetate or thiol is known to produce the respective arabino epimer (Pankiewicz, supra; Kim, supra).

To prepare the corresponding [$^{18}$F] radiolabeled compounds 8b and 9b, the respective triflate precursors 4 and 5 were first fluorinated with n-Bu$_4$N$^{18}$F, which was prepared in situ from n-Bu$_4$NHCO$_3$ and aqueous H[$^{18}$F] to produce compounds 6b and 7b, respectively. The yield was much higher for compound 7b compared to 6b. Unreacted fluoride was removed by passing the crude reaction mixture through a Sep-Pak cartridge (silica) and the product was eluted with 10% methanol in dichloromethane. After solvent evaporation the crude labeled compounds 6b and 7b were easily hydrolyzed with acid, and the desired labeled nucleosides 8b and 9b isolated by high performance liquid chromatography (HPLC) purification using 9% MeCN.

The direct fluorination of the purine nucleoside according to this invention is a convenient and superior to the three-step method in which the fluorinated glycosyl moiety is prepared first, converted to its 1-bromo derivative and then coupled with the purine. This is in contrast to reports of the attempted direct fluorination of pyrimidine analogs, which failed to produce the desired product (Pankiewicz, 1992; Alauddin, et al., *J. Labeled Comp. Radiopharm.*, 45:583-590 (2002)). In addition, the direct fluorination method is suitable for routine production.

II. Methods of Use

The [$^{18}$F]-labeled purine-based nucleoside analog imaging agents of this invention are useful for imaging biological material or for use in imaging-aided applications, including PET imaging. This includes their use as in vivo effective imaging agents for visualizing and/or identifying biological material and for visualizing and/or identifying diseases and pathologies. Diseases involved in this aspect of the invention include ischemic insults such as myocardial or cerebral infarction and space-occupying lesions (e.g., tumors or inflammatory lesions) in solid organs such as the liver, kidney, spleen, adrenal gland, etc. These agents are also useful in the follow-up of a therapy, for instance in development of necrosis and necrosis-related pathologies, such as that caused by pathologic or therapeutically-induced ischemia or originating from trauma, radiation and/or chemicals in organs and tumor tissues.

Accordingly, a further aspect of the present invention provides methods for imaging, detecting, and/or evaluating imaging biological material in vivo using a [$^{18}$F]-labeled purine nucleoside analog of this invention. In one embodiment, the process comprises administering to the subject a sufficient amount of a composition comprising a 2'-deoxy-2'-[$^{18}$F]-labeled or a 3'-deoxy-3'-[$^{18}$F]-labeled purine nucleoside analog to provide an imagable concentration of said analog in said biological material, and detecting the emissions from said radioactive fluorine, thereby forming an image of the biological material. In a preferred embodiment, the imaging agent is a 2'-deoxy-2'-[$^{18}$F]-fluoro-9-β-D-arabinofuranosyl purine analog or a 3'-deoxy-3'-[$^{18}$F]-fluoro-9-β-D-xylofuranosyl purine analog, such as [$^{18}$F]-FAA or [$^{18}$F]-FXA, respectively. In certain instances, the image can be compared to the image obtained from a normal subject in order to assess or diagnose the condition of the biological material.

As used herein, the term "subject" is intended to include human and non-human animals.

As used herein, the term "normal subject" refers to a subject who does not suffer from the particular disease being tested for.

The term "biological material" is meant to comprise every kind of material which has a biological origin. More particularly this term refers to parts of subject such as organ and tissue samples including, but not limited to, organs, parts of organs or systems, including, but not limited to, myocardial tissues, vascular beds, skin, muscle, bone, bone marrow, heart, lung, liver, spleen, pancreas, stomach, brain, intestine, and kidney, including tissues such as for example necrotic tissue, and tumors.

In one embodiment, a sufficient amount of an imaging agent of this invention is combined with a pharmaceutically acceptable carrier for use in imaging studies. In accordance with the invention, "a sufficient amount" of the imaging agent of the invention is defined as an amount sufficient to yield an acceptable image using equipment which is available for clinical use. Sufficient amounts of the imaging agent of the invention will vary according to factors such as the degree of susceptibility of the individual, the age, sex, and weight of the individual, idiosyncratic responses of the individual, and the dosimetry. Sufficient amounts of the imaging agent of the invention will also vary according to instrument and film-related factors. Optimization of such factors is well within the level of skill in the art.

The imaging of tissues (e.g., ischemic, inflamed, injured, infected, or healing organs or tissues) is important for the prediction and/or diagnosis of localized and generalized diseases and disorders and/or organ, tissue, or vessel damage. The invention is not limited to the particular biological material imaged.

For example, imaging myocardial tissue or vascular beds in the coronary arteries or other vascular areas, for example can be useful in predicting the risk of cardiac or vascular disorders. In one embodiment, the vascular disease is selected from the group consisting of atherosclerosis, coronary artery disease (CAD), myocardial infarction (MI), ischemia, stroke, peripheral vascular diseases, and venous thromboembolism. In another embodiment, the methods of predicting risk of a vascular disease or disorder may be used in combination with other known risk factors for vascular diseases or disorders.

The terms "vasculature," "vessels," and "circulatory system" are intended to include all vessels through which blood circulates, including, but not limited to the heart, veins, arteries, arterioles, venules and capillaries.

The term "vascular disease or disorder," also commonly referred to as "cardiovascular disease, coronary heart disease (CHD) and coronary artery disease (CAD)" as used herein, refers to any disease or disorder effecting the vascular system, including the heart and blood vessels. A vascular disease or disorder includes any disease or disorder characterized by vascular dysfunction, including, for example, intravascular stenosis (narrowing) or occlusion (blockage) due to, for example, a build-up of plaque on the inner arterial walls, and diseases and disorders resulting therefrom. Also intended to be within the scope of the invention are thrombotic, or thromboembolic, events. The term "thrombotic or thromboembolic event" includes any disorder that involves a blockage or partial blockage of an artery or vein with a thrombosis. Examples of vascular diseases and disorders include, without limitation, atherosclerosis, CAD, MI, unstable angina, acute coronary syndrome, pulmonary embolism, transient ischemic attack, thrombosis (e.g., deep vein thrombosis, thrombotic occlusion and re-occlusion and peripheral vascular thrombosis), thromboembolism, e.g., venous thromboembolism, ischemia, stroke, peripheral vascular diseases, and transient ischemic attack.

The amount of imaging agent used for diagnostic purposes and the duration of the imaging study will depend upon the nature and severity of the condition being treated, on the nature of therapeutic treatments which the patient has undergone, and on the idiosyncratic responses of the patient.

When used in in vivo assays, an imaging agent according to this invention is administered in an appropriate composition to a subject. Visualization of biological material is possible by detecting emission from the radiolabelled imaging agent using imaging techniques, such as, for instance, Positron Emission Tomography (PET), Single Photon Emission Computerized Tomography (SPECT), and the like. This process of imaging biological material in vivo by administering the imaging agent and detecting the emissions from the imaging agent also constitutes a part of the present invention. The imaging agents of the present invention preferably remain in the biological material for an extended period of time at functionally active concentrations until the agent is metabolized and cleared by the body. As such, multiple images may be taken after a single, low-dose administration of the imaging agent.

Images are generated by virtue of differences in the spatial distribution of the imaging agent which accumulates in the various tissues and organs of the subject. The spatial distribution of the imaging agent accumulated in a mammal, in an organ, or in a tissue may be measured using any suitable means, for example, a gamma camera, a PET apparatus, a SPECT apparatus, and the like. The invention provides for visualization, e.g., detection or imaging, of an imaging agent of this invention using any imaging techniques which are well-known in the art, including positron emission tomography (PET).

As used herein, the term "imaging" or "clinical imaging" refers to the use of any imaging technology to visualize an organ or tumor, either in vivo or ex vivo, by measuring the energy emitted by the tissue or organ after localization of the radioactive agent following administration. Imaging technologies such as positron emission tomography (PET) and the like are applied.

As used herein, "positron emission tomography imaging" or "PET" incorporates all positron emission tomography imaging systems or equivalents and all devices capable of positron emission tomography imaging. The methods of the invention can be practiced using any such device, or variation of a PET device or equivalent, or in conjunction with any known PET methodology. See, e.g., U.S. Pat. Nos. 6,151,377; 6,072,177; 5,900,636; 5,608,221; 5,532,489; 5,272,343; 5,103,098, each of which is incorporated herein by reference. Animal imaging modalities are included, e.g., micro-PETs (Corcorde Microsystems, Inc.).

In another embodiment, the invention relates to a method for generating an image of a biological material, comprising systemically or locally administering to the subject an effective amount of an imaging agent of this invention. "Systemic administration" as used herein means the administration of a composition comprising an imaging agent of this invention such that it enters the subject's system and, thus, is subject to metabolism and other like processes, for example, subcutaneous or intravenous administration.

Alternatively, the imaging agents of the invention are also useful for local administration, e.g., including intracoronary administration in the case of a patient with myocardial infarction. Depending on the specific case, an effective local dose of the contrast agent of the invention may be from 1 to about 5 µmoles of the imaging agent per kg body weight of the subject to be treated.

The in vivo data as described in Examples 2 and 3 demonstrate that $[^{18}F]$-FAA is also a useful agent for imaging tumors. Accordingly, $[^{18}F]$-FAA may also be used in accordance with the methods of the invention by those of skill in the art, e.g., by specialists in nuclear medicine, to image tumors in a subject. Any mammalian tumor may be imaged using the imaging agents of the invention. For example, the imaging agents of the invention are suitable for imaging breast tumors, prostate tumors melanomas, colon tumors, etc.

Some tumors may be evident when a less intense spot appears within the image, indicating the presence of tissue in which a lower concentration of imaging agent accumulates relative to the concentration of imaging agent which accumulates in the tumor. Alternatively, a tumor might be detectable as a more intense spot within the image, indicating a region of enhanced concentration of the imaging agent at the site of the tumor relative to the concentration of agent which accumulates in surrounding tissue. The extent of accumulation of the imaging agent may be quantified using known methods for quantitating radioactive emissions. A particularly useful imaging approach employs more than one imaging agent to perform simultaneous studies.

III. Pharmaceutical Compositions

Another aspect of the present invention provides pharmaceutically-acceptable compositions which comprise an imaging agent of this invention, i.e., a 2'-deoxy-2'-$[^{18}F]$-labeled or a 3'-deoxy-3'-$[^{18}F]$-labeled purine nucleoside analog, formulated with one or more pharmaceutically-acceptable carrier(s) or adjuvant(s), in an amount sufficient to allow imaging of a biological material.

In a particular embodiment, the imaging agent is administered to the subject using a pharmaceutically-acceptable formulation, e.g., a pharmaceutically-acceptable formulation that suitable for administration in liquid form, including parenteral administration, for example, by intravenous injection, either as a bolus or by gradual infusion over time, intraperitoneally, intramuscularly, intracavity, subcutaneously, or directed directly into the vascular tissue of interest as, for example, a sterile solution or suspension.

The phrase "pharmaceutically acceptable" is employed herein to compositions containing an imaging agent of this invention, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from organ, or portion of the body, to another organ, or portion of the body. Each carrier must be "acceptable" in the sense of being compatible with the other ingredients of the formulation and not injurious to the subject. Examples of suitable aqueous and non-aqueous materials which can serve as pharmaceutically-acceptable carriers include, but are not limited to: pyrogen-free water; isotonic saline; Ringer's solution; ethyl alcohol; phosphate buffer solutions; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as poloxamer 338 and polyethylene glycol 1450; oils, such as peanut oil, cottonseed oil, safflower oil, sesame oil, olive oil, corn oil, and soybean oil; polyols, such as glycerin, sorbitol mannitol, propylene glycol polyethylene glycol, and the like; esters, such as ethyl oleate and ethyl laurate; agar; buffering agents, such as magnesium hydroxide and aluminum hydroxide; alginic acid; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Methods of preparing these compositions include the step of bringing an imaging agent of this invention into association with the carrier and, optionally, one or more accessory ingredients. Usually, the formulations are prepared by uniformly and intimately bringing into association the imaging agent with liquid carriers.

Pharmaceutical compositions of this invention suitable for parenteral administration comprise one or more contrast agent(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms of an imaging agent of this invention can be made by forming microencapsule matrices of the agent in biodegradable polymers such as polylactide-polyglycolide. Depending on the ratio of agent to polymer, and the nature of the particular polymer employed, the rate of agent release can be controlled. Examples of other biodegradable polymers include poly(orthoesters) and poly(anhydrides). Depot injectable formulations are also prepared by entrapping the agent in liposomes or microemulsions which are compatible with body tissue.

Suspensions, in addition to an imaging agent of this invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by combining an imaging agent of this invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Compositions of the present invention which are suitable for vaginal administration also include pessaries, tampons, creams, gels, pastes, foams or spray formulations containing such carriers as are known in the art to be appropriate.

The term "administration" or "administering" is intended to include routes of introducing an imaging agent of this invention to a subject to perform their intended function. Examples of routes of administration which can be used include, for example, injection (subcutaneous, intravenous, parenterally, intraperitoneally, intrathecal. The pharmaceutical preparations are, of course, given by forms suitable for each administration route. For example, these preparations are administered, for example, by injection. The injection can be bolus or can be continuous infusion. Depending on the route of administration, the imaging agent can be coated with or disposed in a selected material to protect it from natural conditions which may detrimentally effect its ability to perform its intended function. The imaging agent can be administered alone, or in conjunction with either another agent or with a pharmaceutically-acceptable carrier, or both. The imaging agent can be administered prior to the administration of the other agent, simultaneously with the agent, or after the administration of the agent. Furthermore, the imaging agent can also be administered in a prodrug form which is converted into its active metabolite, or more active metabolite in vivo.

The phrases "parenteral administration" and "administered parenterally" as used herein means modes of administration other than enteral and topical administration, usually by injection, and includes, without limitation, intravenous, intramuscular, intraarterial, intrathecal intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Preferably, if an imaging agent of this invention is administered intravenously, it will be formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain, in addition to the imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

To use an imaging agent of this invention according to the present invention, the imaging agent is given in a dose which is diagnostically effective. A "diagnostically effective amount" or "effective amount" of an imaging agent of this invention is typically an amount such that when administered in a physiologically tolerable composition is sufficient to enable detection of organs, tissues, or tumors.

In one embodiment, compositions comprising an imaging agent of this invention are administered intravenously, as by injection of a unit dose, for example. The term "unit dose" when used in reference to the imaging agent refers to physically discrete units suitable as unitary dosage for the subject, each unit containing a predetermined quantity of active material calculated to produce the desired effect in association with the required diluent, i.e., carrier, or vehicle. The amount of agent which can be combined with a carrier material to produce a single dosage form will vary depending upon the host being treated, the particular mode of administration. The amount of agent which can be combined with a carrier material to produce a single dosage form will generally be that amount of the compound which produces a desired effect.

An imaging agent of this invention is administered in a manner compatible with the dosage formulation, and in an effective amount. The quantity to be administered depends on the subject, capacity of the subject's system to utilize the active ingredient, the degree of contrast desired, and the structure to be imaged. Precise amounts of the imaging agent to be administered depend on the judgment of the practitioner and are peculiar to each individual. However, suitable dosage ranges for systemic application are disclosed herein and depend on the route of administration. Suitable regimes for initial administration and subsequent administration, e.g., after initial imaging, are also contemplated and are typified by an initial administration followed by repeated doses at one or more hour intervals by a subsequent injection or other administration. Bolus administration, multiple dosages or continuous intravenous infusion sufficient to maintain concentrations in the blood in the ranges for specific in vivo imaging are also contemplated. Infusion of the imaging agent may be for less than one minute, two minutes, three minutes, four minutes, five minutes, or more.

IV. Kits

The imaging agents of the invention can be incorporated into a commercial kit or system for imaging organ tissues (e.g., myocardial tissues and other organ tissues), and tumors. The kit may contain an imaging agent of this invention, e.g., [$^{18}$F]-FAA or [$^{18}$F]-FXA, and instructions for use and may further contain directions on the administration and use of the imaging agent in conjunction with the appropriate imaging technology and dosage requirement for the intended use.

The specific activities of the radiolabeled [$^{18}$F]-FAA and [$^{18}$F]-FXA prepared in accordance with the present invention will generally range from about 50 to about 100 Ci/mmol. Between 50-100 μg of unlabeled [$^{18}$F]-FAA or [$^{18}$F]-FXA would be administered intravenously into humans using 20 mCi doses of material with this specific activity, although somewhat larger or smaller doses may be appropriate in particular instances, as would be appreciated by those working in the field. For example, the half-life of $^{18}$F is about 110 minutes. Accordingly, a unit dose of about 5 to 20 mCi [$^{18}$F]-FAA or [$^{18}$F]-FXA would be sufficient. Administration of the agents and their use in imaging (for example, using positron emission tomography) would be routine for those skilled in the imaging art.

The invention is further illustrated by the following non-limiting examples. All scientific and technical terms have the meanings as understood by one with ordinary skill in the art. The specific examples which follow illustrate the methods in which the compositions of the present invention may be prepared and used and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

Reagents and Instrumentation

All reagents and solvents were purchased from Aldrich Chemical Co. (Milwaukee, Wis.), and used without further purification. Solid phase extraction cartridges (Sep-Pak) were purchased from Waters Associates (Milford, Mass.). Thin layer chromatography (TLC) was performed on pre-coated Kieselgel 60 F254 (Merck) glass plates. Proton and $^{19}$F NMR spectra were recorded on a Brucker 360 MHz or 500 MHz spectrometer using tetramethylsilane as an internal reference and hexafluorobenzene as an external reference, respectively. Mass spectra were obtained on a Finnigan 400 mass spectrometer at the University of Minnesota using the ammonia chemical ionization technique. High performance liquid chromatography (HPLC) was performed on a system using a 510 pump (Waters Associates, Milford, Mass.), UV detector (Isco, Lincoln, Nebr.) operated at 254 nm, and a radioactivity detector with single-channel analyzer (Technical Associate, Woodland Hills, Calif.) using a semi-preparative C18 reverse phase column (Alltech, Econosil, 10×250 mm, Deerfield, Ill.) and an analytical C18 column (Alltech, Econosil 4.6×250 mm). An acetonitrile/water (MeCN/H$_2$O) solvent system (9% MeCN) was used for purification of the radiolabeled nucleosides and quality control analysis.

Example 1

Synthesis of unlabeled and labeled 2'-Fluoro-9-β-D-arabinofuranosyladenine and 3'-fluoro-9-β-D-xylo-furanosyladenine $N^6$,3',5'-Tri-methoxytrityl-2'-hydroxy-9-β-D-ribo-furanosyladenine (2) and $N^6$,2',5'-tri-methoxytrityl-3'-hydroxy-9-β-D-ribofuranosyladenine (3)

Compounds 2 and 3 were prepared following a literature method (Pankiewicz, et al., *J. Org. Chem.*, 1992; 57:553-559). Briefly, adenosine 1.35 g (5.0 mmol), dimethylaminopyridine 0.5 g (1 equiv.), methoxytrityl chloride 5.45 g (17.6 mmol) were placed in a dry flask under argon. Pyridine (80 mL) was added and the mixture was heated with stirring at 85-88° C. for 18 hours, after which TLC showed no significant starting material remained. Solvent was evaporated under vacuum, the residue was dissolved in 50% EtOAc/hexane and the solution washed with water. The organic phase was evaporated to dryness and purified by column chromatography using 25% ethyl acetate in hexane. Pure compounds 2 and 3 were isolated in 28% and 50% yields, respectively.

Compound 2: $^1$H NMR (DMSO-D$_6$): δ 8.27 (s, 1H, C$_8$H), 7.78 (s, 1H, C$_2$H), 6.74-7.31 (m, 42H, aromatic), 6.09 (d, 1H, J=7.25 Hz, 1'H), 5.99 (d, 1H, J=6.75 Hz, OH, exchangeable with D$_2$O), 4.88 (m, 1H, 2'H), 4.13 (d, 1H, J=4.1 Hz, 3'H), 3.71 (s, 3H, OMe), 3.70 (s, 3H, OMe), 3.66 (s, 3H, OMe), 3.09 (bs, 1H, 4'H), 2.63 (bs, 2H, 5'H).

Compound 3: $^1$H NMR (DMSO-D$_6$): δ 8.06 (s, 1H, C$_8$H), 7.65 (s, 1H, C$_2$H), 6.60-7.32 (m, 42H, aromatic), 5.87 (d, 1H, J=5.85 Hz, 1'H), 4.98 (m, 2H, 2'H and OH, exchangeable with D$_2$O), 3.99 (bs, 1H, 3'H), 3.70 (s, 3H, OMe), 3.69 (s, 3H, OMe), 3.63 (s, 3H, OMe), 3.29 (bs, 1H, 4'H), 3.08 (m, 1H, 5'aH), 2.9 (m, 1H, 5'bH).

$N^6$,3',5'-Tri-methoxytrityl-2'-trifluoromethanelsulfo-nyl-9-β-D-ribofuranosyladenine (4) and $N^6$,2',5'-tri-methoxytrityl-3'-trifluoromethanesulfonyl-9-β-D-ribofuranosyladenine (5)

Compounds 4 and 5 were each prepared by the following representative procedure. Compound 2 or 3 (0.55 g, 0.5 mmol) was dissolved in pyridine (7 mL) under argon and cooled in ice bath. Trifluoromethanesulfonic acid anhydride (0.2 mL, 1.3 equiv) was added and the reaction mixture was stirred for 10 minutes in the cold and subsequently for 30 minutes at room temperature. The reaction mixture was quenched with cold water and extracted with 50% EtOAc/hexane. The organic extract was evaporated to dryness and purified by chromatography on a silica gel column using 30% ethyl acetate in hexane. Pure compound (560 mg) was obtained in 90% yield.

Compound 4: $^1$H NMR (DMSO-$D_6$): δ 8.38 (s, 1H, $C_8$H), 7.62 (s, 1H, $C_2$H), 6.74-7.40 (m, 42H, aromatic), 6.62 (d, 1H, J=4.25 Hz, 1'H), 5.93 (t, 1H, J=5.0 Hz, 2'H), 4.50 (t, 1H, J=4.3 Hz, 3'H), 3.81 (bs, 1H, 4'H), 3.71 (s, 3H, OMe), 3.70 (s, 3H, OMe), 3.65 (s, 3H, OMe), 2.87-2.93 (m, 2H, 5'H). $^{19}$F NMR (δ): −73.16 (s). High resolution MS: M$^+$, Calculated 1215.4064; found 1215.4028.

Compound 5: $^1$H NMR (DMSO-$D_6$): δ 8.46 (s, 1H, $C_8$H), 6.64-7.40 (m, 43H, aromatic and $C_2$H), 6.43 (d, 1H, J=8.1 Hz, 1'H), 6.04 (m, 1H, 3'H), 4.26 (d, 1H, J=4.1 Hz, 4'H), 4.13 (m, 1H, 2'H), 3.72 (s, 3H, OMe), 3.65 (s, 3H, OMe), 3.58 (s, 3H, OMe), 2.9 (m, 2H, 5'H). $^{19}$F NMR (δ) −73.58 (s). High resolution MS: M$^+$ Calculated 1215.4064; found 1215.4034.

$N^6$,3',5'-Tri-methoxytrityl-2'-fluoro-9-β-D-arabino-furanosyl-9-β-D-xylofuranosyladenine (6a) and $N^6$,2',5'-tri-methoxytrityl-3'-fluoro-9-β-D-xylofuranosyladenine (7a)

Compound 4 or 5 (30 mg) was dissolved in dry MeCN (1.5 mL) in a sealed V-vial. To this solution n-$Bu_4$NF (1M, 30 μL) was added and the mixture was heated for 30 minutes at 72-74° C. in a heating block. The reaction mixture was cooled to room temperature, the solvent evaporated in a stream of air and the residue purified on a short silica gel column using 30% ethyl acetate in hexane. Pure compound 6 (5 mg) or 7 (12 mg) were obtained in 20% and 50% yields, respectively.

Compound 6a: $^1$H NMR (DMSO-$D_6$): δ 7.87 (s, 1H, $C_2$H), 7.83 bs, 1H, $C_8$H), 6.74-7.40 (m, 42H, aromatic), 6.40 (dd, 1H, J=24 Hz and 2.1 Hz, 1'H), 4.4 (m, 1H, 4'H), 4.22-4.38 (m, 2H, 2'H and 3'H), 3.71 (s, 3H, OMe), 3.70 (s, 3H, OMe), 3.65 (s, 3H, OMe), 3.01-3.12 (m, 2H, 5'H). $^{19}$F NMR (δ): −193.95-194.18 (m). High resolution MS: M+H, Calculated 1085.45276; found 1085.45402.

Compound 7a: $^1$H NMR (DMSO-$D_6$): δ 8.10 (s, 1H, $C_8$H), 7.65 (s, 1H, $C_2$H), 6.64-7.40 (m, 42H, aromatic), 6.41 (s, 1H, 1'H), 4.39, (d, J=14.0 Hz, 2'H), 4.24 (dt, J=3.31 Hz and 6.0 Hz, 4'H), 3.82 (d, J=50.6 Hz, 1H, 3'H), 3.78 (s, 6H, OMe), 3.68 (s, 3H, OMe), 3.42-3.45 (m, 1H, 5'aH), 3.28-3.30 (m, 1H, 5'bH). $^{19}$F NMR (δ): −202.57, (dq). High resolution MS: M$^+$, Calculated 1085.45276; found 1085.44915.

2'-Fluoro-9-β-D-arabinofuranosyladenine (8a) and 3'-fluoro-9-β-D-xylofuranosyladenine (9a)

Unlabeled compounds 8a and 9a were prepared by acid hydrolysis of the protecting groups from the respective methoxytrityl derivatives 6a and 7a in 80% yields, following the method reported by Alauddin et al. (*J. Fluorine. Chem.*, 2000; 87:87-91). The products were characterized by $^1$H NMR spectroscopy.

2'-[$^{18}$F]-Fluoro-9-β-D-arabinofuranosyladenine (8b) and 3'-[$^{18}$F]-fluoro-9-β-D-xylofuranosyladenine (9b)

[$^{18}$F]-Labeled compounds were prepared as follows: Aqueous H$^{18}$F (0.4 mL) was added to a solution of n-$Bu_4$NHCO$_3$ (50 μL, 4% by wt.) in a V-vial and the solution evaporated azeotropically to dryness with acetonitrile (1.0 mL) at 72-74° C. under a stream of argon. To the dry residue, n-$Bu_4$N$^{18}$F, a solution of either compound 4 or 5 (1.5-2.0 mg, 1.2-1.6 μmol) in dry acetonitrile (0.5 mL) was added, and the reaction mixture was heated at 72-74° C. for 30 minutes. The reaction mixture was cooled to room temperature, passed through a Sep-Pak cartridge (silica gel), and eluted with 10% methanol in dichloromethane (2.5 mL). After evaporation of the solvent with a stream of argon at ~73° C., the residue was dissolved in methanol. 2N Hydrochloric acid solution in methanol (0.1 mL) was added and the mixture was refluxed for 5 minutes. The crude mixture was neutralized with 1N bicarbonate (0.2 mL), diluted with HPLC solvent (1 mL) and purified by HPLC. The desired product was isolated and the solvent evaporated under vacuum. The residue was re-dissolved in sterile saline and the solution filtered through 0.22 micron Millipore filter (Millipore Corp, Bedford, Mass.) and collected into a sterile pyrogenic vial. The product was co-injected with an authentic unlabeled sample onto an analytical column to confirm its identity. Sterility and pyrogenicity tests were performed on the final preparations after the radioactivity had decayed. The pyrogenicity test was performed using LAL reagent and *E. coli* endotoxin type 055:B5, and the sterility test was performed using thioglycollate and trypticase media.

Figure 2:
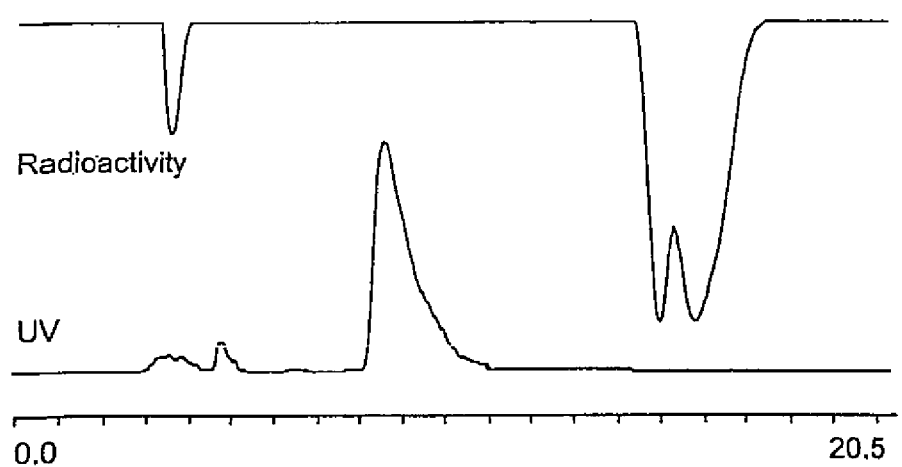
FIG. 2 shows the HPLC chromatogram from the purification of [$^{18}$F]-FAA.

FIG. 2 represents a typical chromatogram obtained during the purification of [$^{18}$F]-FAA (semi-prep column; 9% MeCN/H$_2$O; flow rate=3.375 mL/min; capacity factor=4). The UV peak at 9 minutes corresponds to the by-product, 2'-hydroxy-arabino-adenosine, and the radioactive peak between 15-16 minutes is the desired [$^{18}$F]-FAA. The apparent split of the radioactive peak is an artifact due to the saturation of the detector.

Figure 3:
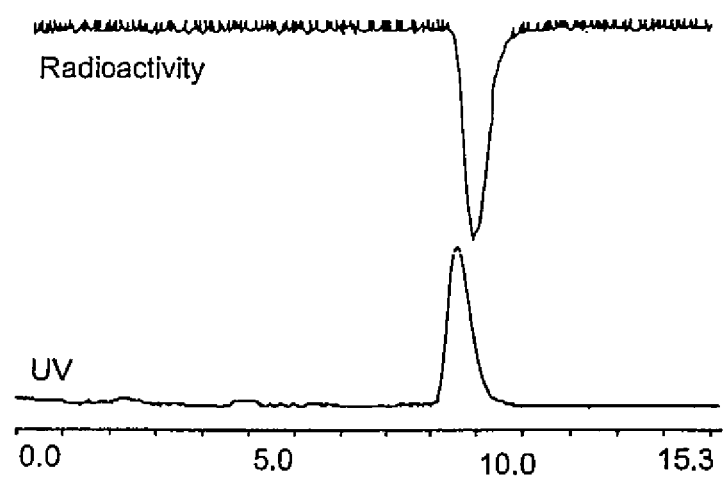
FIG. 3 is an HPLC chromatogram of [$^{18}$F]-FAA.

The radiochemical yield of this synthesis was 10-18% (d.c.) for 8 and 30-48% for 9. The radiochemical purity was >99% with specific activity >74 GBq/μmol. The synthesis time was 90-95 minutes from the end of bombardment (EOB). In representative syntheses, 518 MBq of labeled product 8 was obtained starting from 6.88 GBq of [$^{18}$F]-fluoride, and 3.07 GBq of 9 was obtained from 8.54 GBq of [$^{18}$F]-fluoride. FIG. 3 is an HPLC chromatogram of an analytical sample of [$^{18}$F]-FAA (8), co-injected with standard FAA (analytical C18 column; 9% MeCN/H$_2$O; flow rate=1.13 mL/min). The chromatogram shows a single radioactive peak that co-eluted with an authentic sample.

The radiochemical yields were 10-12% decay corrected (d.c.) for [$^{18}$F]-FAA and 30-35% (d.c.) for [$^{18}$F]-FXA, respectively. Radiochemical purity was >99% and specific activity was >74 GBq/μmol at the end of synthesis (EOS).

Example 2

In Vivo Studies

In vivo studies including biodistribution on tumor-bearing nude mice were conducted at 2 hours post-injection. Tumors were grown in six weeks old athymic nude mice (Harlen-plague-Dawley) by inoculation of approximately 5 million cells (non-transduced) under the skin in the left flank and 8 million cells (transduced) on the right flank. When the tumor was about 1 cm in size, animals were used for the experiment as described below.

One group of mice (n=5) were injected intravenously via a tail vein with [$^{18}$F]-FAA (~20 μCi, 200 μL). Another group of mice were injected with [$^{18}$F]-FXA (~20 μCi, 200 μL). Activity injected into each mouse was measured in a dose calibrator (Capintec). Blood samples were taken by a capillary tube (1.33 μL) from the contralateral tail vein after rupture with a needle at different time intervals (1, 2, 5, 10, 20, 40, 60 and 120 minutes). Activity in each blood sample was measured by a gamma counter, standardized for injected dose, and % injected dose per gram was calculated. Mean % injected dose per gram was plotted against time to obtain the blood clearance curve for each compound. Animals were anesthetized with Nembutal (40 mg/kg) and sacrificed at 2 hours post-injection. All organs including tumor were separated and weighed. Radioactivity in each organ was measured using a gamma counter. For each mouse, radioactivity uptake was expressed as % injected dose per gram, and as ratio of organ to blood uptake. From these data, the mean and standard deviation were calculated for each group.

Figure 4:
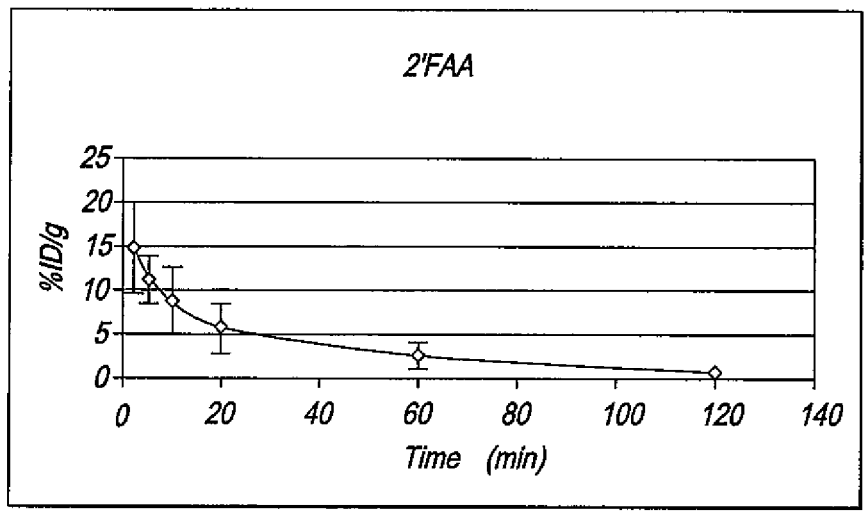
FIG. 4 is a blood clearance curve for [$^{18}$F]-FAA.
Figure 5:
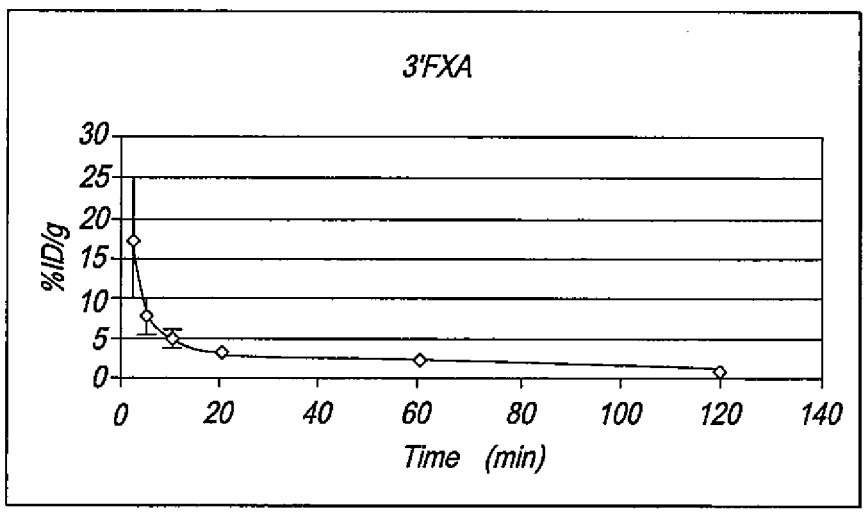
FIG. 5 is a blood clearance curve for [$^{18}$F]-FXA.

FIGS. 4 and 5 are blood clearance curves of [$^{18}$F]-FAA and [$^{18}$F]-FXA, respectively. The curves show that both compounds have similar clearance pattern, and clear rapidly from the blood initially, then slow down after 20 minutes post-injection. Fast clearance may have some advantage in PET imaging with these radiotracers.

Table 1 represents biodistribution of [$^{18}$F]-FAA and [$^{18}$F]-FXA, shown as % ID/g of radiotracers in organs and tumors at 2 hours. The biodistribution data shows that uptake of [$^{18}$F]-FAA in tumors compared to blood was 3.3-fold higher. Maximum amount (11.65% ID/g) of [$^{18}$F]-FAA was accumulated in spleen, which is the highest incorporating tissue. Uptake of this tracer in liver and kidney was also high, 2.4% and 3.5%, respectively. Both transduced and non-transduced cells were used to grow tumors on the same animal in order to determine any biochemical reactions of the compound with herpes simplex virus thymidine kinase (HSV-tk). Tumor uptake in both transduced and wild type cells were comparable, which suggests that this tracer is not a substrate for HSV-tk. Tumor uptake of [$^{18}$F]-FAA is consistent with that reported for 2-chloro-2'-arabinofluoro-2'-deoxyadenosine (Carson, et al., Proc. Natl. Acad. Sci. USA, 89:2970-2974 (1992)). Although uptake in organs was high, tumor uptake was more than 3-fold higher than the background activity. Specific accumulation of [$^{18}$F]-FAA in spleen suggests that the target may have some receptors specific for this compound.

In contrast to [$^{18}$F]-FAA, the biodistribution of [$^{18}$F]-FXA was quite different. Highest uptake of [$^{18}$F]-FXA was in the heart followed by liver and kidney. Heart tissue is known to have adenosine receptors, which possibly suggests that this compound has similar receptor binding property as adenosine. Compared to the background activity, muscle uptake was also slightly higher. Both [$^{18}$F]-FAA and [$^{18}$F]-FXA have higher uptake in liver and kidney. There was no significant uptake of [$^{18}$F]-FXA in tumors (tumor/blood ratio was less than 1)

TABLE 1

| Organ | % ID/g* [$^{18}$F]-FAA | Organ/blood [$^{18}$F]-FAA | % ID/g* [$^{18}$F]-FXA | Organ/blood [$^{18}$F]-FXA |
|---|---|---|---|---|
| Blood | 0.532 ± 0.087 | 1.00 | 1.034 ± 0.157 | 1.00 |
| Skin | 1.032 ± 0.214 | 1.94 | 0.452 ± 0.146 | 0.43 |
| Muscle | 0.748 ± 0.152 | 1.41 | 2.430 ± 0.332 | 2.31 |
| Bone + marrow | 0.908 ± 0.377 | 1.71 | 1.844 ± 0.479 | 1.78 |
| Heart | 1.548 ± 0.175 | 2.91 | 8.430 ± 1.883 | 8.15 |
| Lung | 1.436 ± 0.311 | 2.69 | 1.000 ± 0.401 | 0.96 |
| Liver | 2.433 ± 0.661 | 4.57 | 6.934 ± 1.207 | 6.70 |
| Spleen | 11.649 ± 2.698 | 21.89 | 0.764 ± 0.160 | 0.74 |
| Pancreas | 0.952 ± 0.158 | 1.79 | 1.507 ± 0.334 | 1.45 |

TABLE 1-continued

| Organ | % ID/g* [$^{18}$F]-FAA | Organ/blood [$^{18}$F]-FAA | % ID/g* [$^{18}$F]-FXA | Organ/blood [$^{18}$F]-FXA |
|---|---|---|---|---|
| Stomach | 1.117 ± 0.197 | 2.09 | 0.461 ± 0.143 | 0.44 |
| Intestine | 1.926 ± 0.384 | 3.62 | 0.726 ± 0.319 | 0.70 |
| Kidney | 3.472 ± 0.500 | 6.52 | 6.394 ± 1.241 | 6.12 |
| Tumor (wild) | 1.743 ± 0.242 | 3.27 | 0.673 ± 0.168 | 0.65 |
| Tumor (tk+) | 1.554 ± 0.196 | 2.92 | 0.489 ± 0.075 | 0.47 |

*Average of 5 animals ± SD

Figure 6:
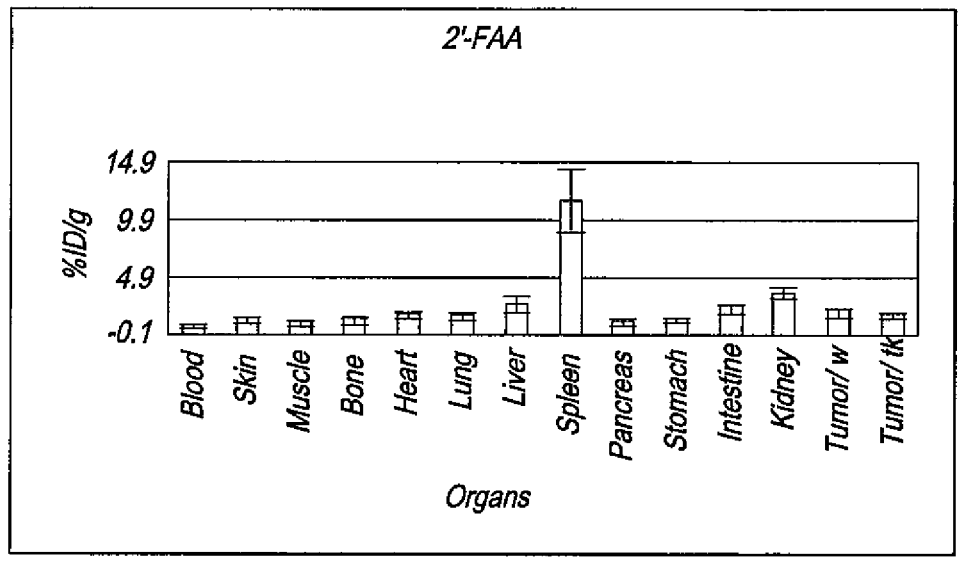
FIG. 6 is a graphical representation of biodistribution of [$^{18}$F]-FAA.
Figure 7:
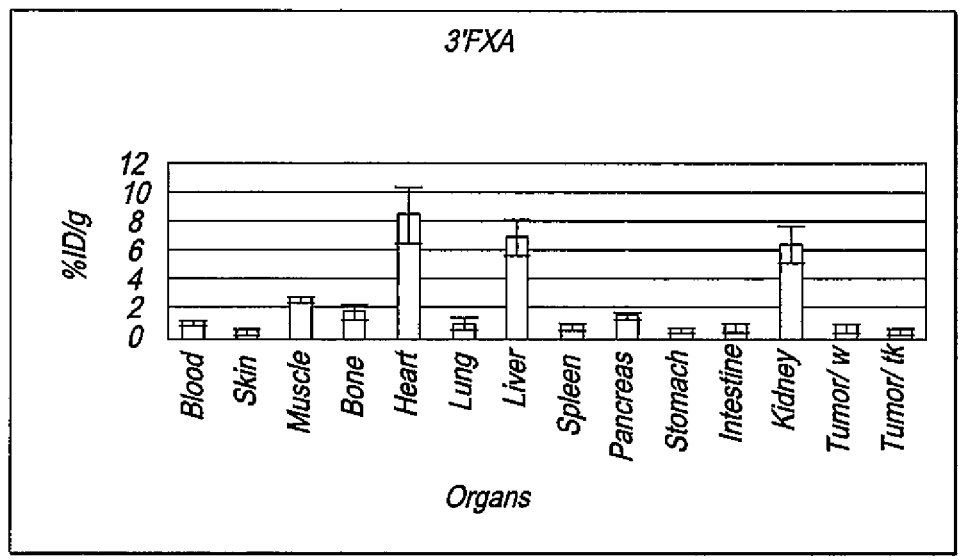
FIG. 7 is a graphical representation of biodistribution of [$^{18}$F]-FXA.

FIGS. 6 and 7 are graphical representations of the biodistribution of [$^{18}$F]-FAA and [$^{18}$F]-FXA, respectively. As shown in FIG. 6, [$^{18}$F]-FAA is selectively accumulated into spleen. Both tumors have higher uptake of [$^{18}$F]-FAA than blood. [$^{18}$F]-FXA uptake is dominated in heart followed by liver and kidney.

Example 3

PET Imaging Studies

For PET imaging studies, animals were injected with either [$^{18}$F]-FAA or [$^{18}$F]-FXA approximately 0.2 mCi activity through tail vein. PET imaging was performed using a Micro-PET scanner (Concorde Microsystems, Inc.), with 120 transaxial planes and spatial resolution of 2.0 mm, at 30 minutes, 1 hour and 2 hours post-injection. Images were reconstructed using Ordered Subset Expectation Maximization (OSEM) algorithm.

Figure 10:
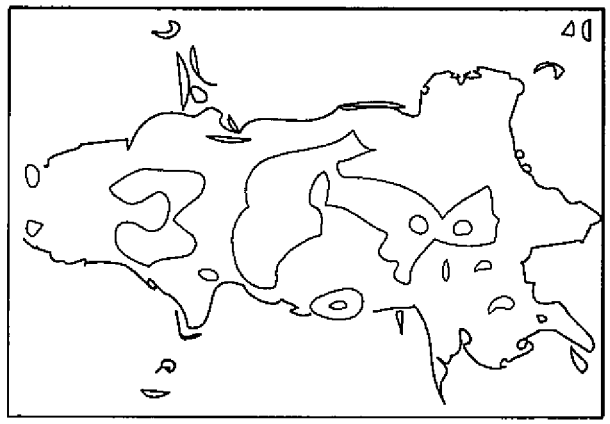
FIG. 10 is a coronal micro-PET image of [$^{18}$F]-FAA at 2 hours post-injection.
Figure 9:
FIG. 9 is a coronal micro-PET image of [$^{18}$F]-FAA at 1 hour post-injection.
Figure 8:
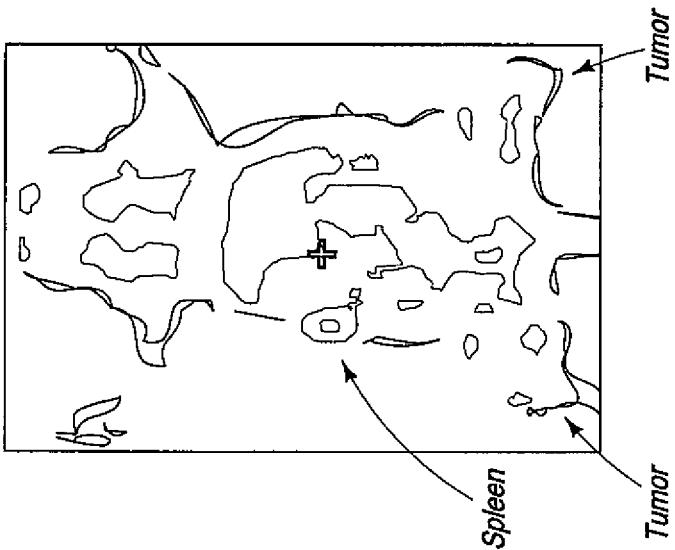
FIG. 8 is a coronal micro-PET image of [$^{18}$F]-FAA at 30 minutes post-injection.

FIGS. 8, 9, and 10 are coronal micro-PET images of [$^{18}$F]-FAA at 30 minutes, 1 hour and 2 hours post-injection, respectively. In agreement with the biodistribution results, micro-PET images also demonstrate high uptake in spleen. Tumors in both flanks are visible compared to background activity. There is no significant difference in images at these time points, possibly suggesting that wash out of activity with time was minimal, i.e., the activity accumulated in the tissue or tumor within 30 minutes is retained with time.

Figure 13:
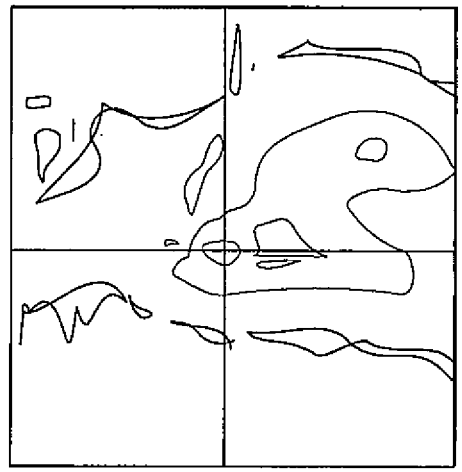
FIG. 13 is a sagittal micro-PET image of [$^{18}$F]-FXA in heart at 2 hours post-injection.
Figure 12:
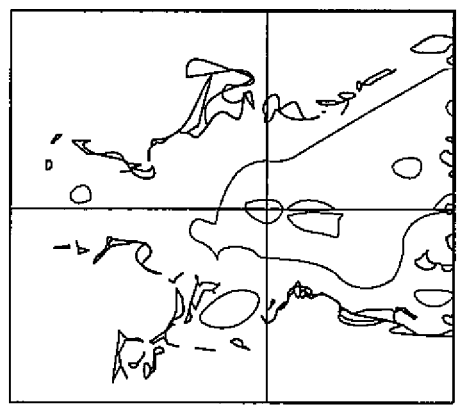
FIG. 12 is a coronal micro-PET image of [$^{18}$F]-FXA in heart at 2 hours post-injection.
Figure 11:
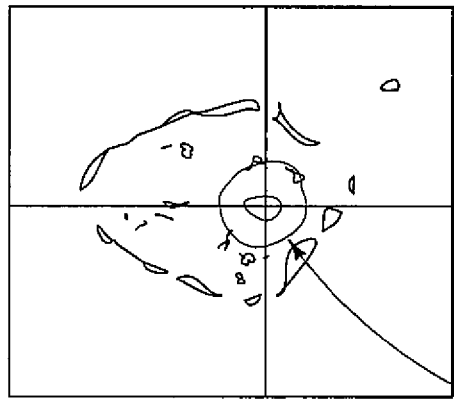
FIG. 11 is a transaxial micro-PET image of [$^{18}$F]-FXA in heart at 2 hours post-injection.

FIGS. 11, 12, and 13 are transaxial, coronal and sagittal micro-PET images of [$^{18}$F]-FXA, respectively, in heart at 2 hours post-injection. The transaxial PET image suggests that [$^{18}$F]-FXA derived activity is in the heart, and this activity did not wash out in 2 hours post-injection. This image is in agreement with the biodistribution results.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims. All references cited herein are incorporated by reference in their entirety. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A composition for in vivo imaging of a biological material, comprising:
    an imaging agent in dosage unit form, wherein the unit dose of the imaging agent comprises a sufficient amount for in vivo diagnostic imaging of a 2'-deoxy-2'-[$^{18}$F]-labeled or a 3'-deoxy-3'-[$^{18}$F]-labeled purine nucleoside analog for being detected in vivo; and
    a physiologically acceptable carrier or adjuvant.

2. The composition of claim 1, wherein said analog is a 2'-deoxy-2'-[$^{18}$F]-fluoro-9-β-D-arabinofuranosyl purine analog or a 3'-deoxy-3'-[$^{18}$F]-fluoro-9-β-D-xylofuranosyl purine analog.

3. The composition of claim 2, wherein said 2'-deoxy-2'-[$^{18}$F]-fluoro-9-β-D-arabinofuranosyl purine analog is 2'-deoxy-2'-[$^{18}$F]-fluoro-9-β-D-arabinofuranosyladenine.

4. The composition of claim 2, wherein said 3'-deoxy-3'-[$^{18}$F]-fluoro-9-β-D-xylofuranosyl purine analog is 3'-deoxy-3'-[$^{18}$F]-fluoro-9-β-D-xylofuranosyladenine.

5. An in vivo method for imaging a biological material in a subject, comprising:
   administering to said subject a sufficient amount of a composition comprising a 2'-deoxy-2'-[$^{18}$F]-labeled or a 3'-deoxy-3'-[$^{18}$F]-labeled labeled purine nucleoside analog to provide an imagable concentration of said analog in said biological material; and
   detecting emissions from said radioactive fluorine of said analog, thereby forming an image of said biological material.

6. The method of claim 5, wherein said analog is a 2'-deoxy-2'-[$^{18}$F]-fluoro-9-β-D-arabinofuranosyl purine analog or a 3'-deoxy-3'-[$^{18}$F]-fluoro-9-β-D-xylofuranosyl purine analog.

7. The method of claim 6, wherein said 2'-deoxy-2'-[$^{18}$F]-fluoro-9-β-D-arabinofuranosyl purine analog is 2'-deoxy-2'-[$^{18}$F]-fluoro-9-β-D-arabinofuranosyladenine.

8. The method of claim 6, wherein said 3'-deoxy-3'-[$^{18}$F]-fluoro-9-β-D-xylofuranosyl purine analog is 3'-deoxy-3'-[$^{18}$F]-fluoro-9-β-D-xylofuranosyladenine.

9. The method of claim 7, wherein said biological material is a tumor.

10. The method of claim 5, wherein said biological material is an organ or tissue.

11. The method of claim 10 wherein said organ or tissue is myocardial tissues, vascular beds, skin, muscle, bone, bone marrow, heart, lung, liver, spleen, pancreas, stomach, brain, intestine, or kidney.

12. The method of claim 5, wherein said detecting is by positron emission tomography.

13. The method of claim 5, wherein said analog is administered intravenously or intra-arterially.

14. The method of claim 5, wherein said analog is administered at more than one time point.

15. The method of claim 5, wherein said analog is administered by infusion over a period of about five minutes or more.

16. The method of claim 5, wherein said composition further comprises a pharmaceutically acceptable carrier.

17. A method for imaging a tumor in a patient, the method comprising:
   administering to a patient an composition comprising [$^{18}$F]-FAA in an amount sufficient to provide an imagable concentration of said [$^{18}$F]-FAA; and
   detecting emissions from said radioactive fluorine of said [$^{18}$F]-FAA, thereby forming an image of said tumor.

18. The method of claim 17 wherein the detecting is by positron emission tomography.

* * * * *